United States Patent [19]
Chen

[11] Patent Number: 6,120,475
[45] Date of Patent: Sep. 19, 2000

[54] INFUSION BOTTLE MONITOR DEVICE

[76] Inventor: San-Ming Chen, 58, Ma Yuan West St., Taichung, Taiwan

[21] Appl. No.: 09/024,013

[22] Filed: Feb. 16, 1998

[51] Int. Cl.[7] .................................................. A61M 31/00
[52] U.S. Cl. .............................. 604/65; 604/250; 604/253
[58] Field of Search ..................................... 604/250, 253, 604/251, 65–67; 73/861.41

[56] References Cited

U.S. PATENT DOCUMENTS

| | | |
|---|---|---|
| 4,105,028 | 8/1978 | Sadlier et al. . |
| 4,493,710 | 1/1985 | King et al. . |
| 4,718,896 | 1/1988 | Arndt et al. . |
| 4,725,269 | 2/1988 | Danby et al. . |
| 4,808,161 | 2/1989 | Kamch . |
| 5,423,746 | 6/1995 | Burkett et al. . |

*Primary Examiner*—Mark Bockelman

[57] ABSTRACT

An infusion bottle monitor device has an electric circuit module, a sensing module, and a wire connected to the electric circuit module and the sensing module. The electric circuit module has a microprocessing system. The sensing module has a sensing system to output a sensing signal into the microprocessing system. A micromotion control system is disposed in the electric circuit module. A hose is connected to a hollow tube. The hollow tube is connected to an infusion bottle. The sensing module is disposed on the hollow tube. A plurality of clamp devices are disposed on a lateral of the electric circuit module. An opening is formed on the lateral of the electric circuit module. A support frame is disposed on the lateral of the electric circuit module pivotally.

1 Claim, 8 Drawing Sheets

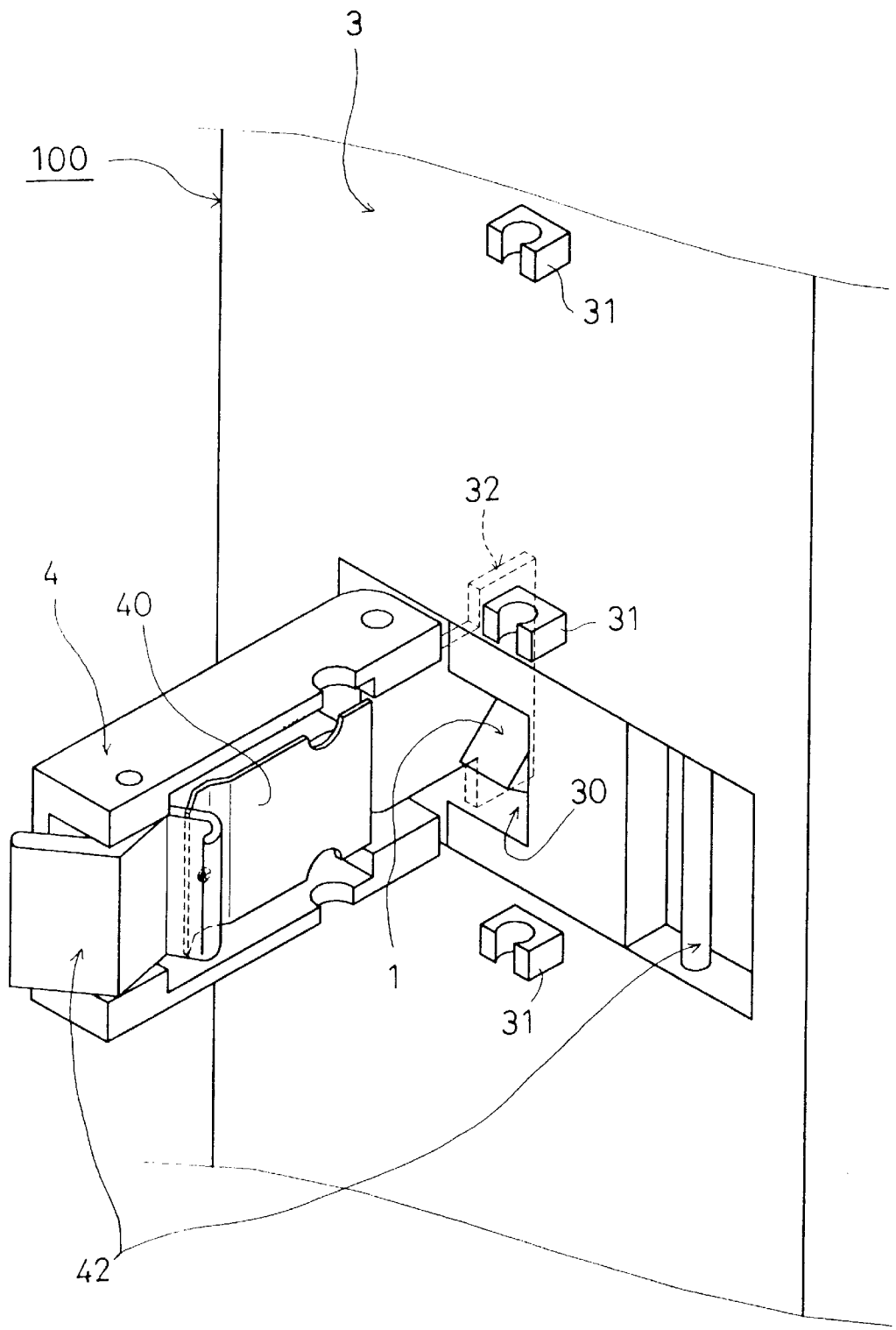
F I G. 3

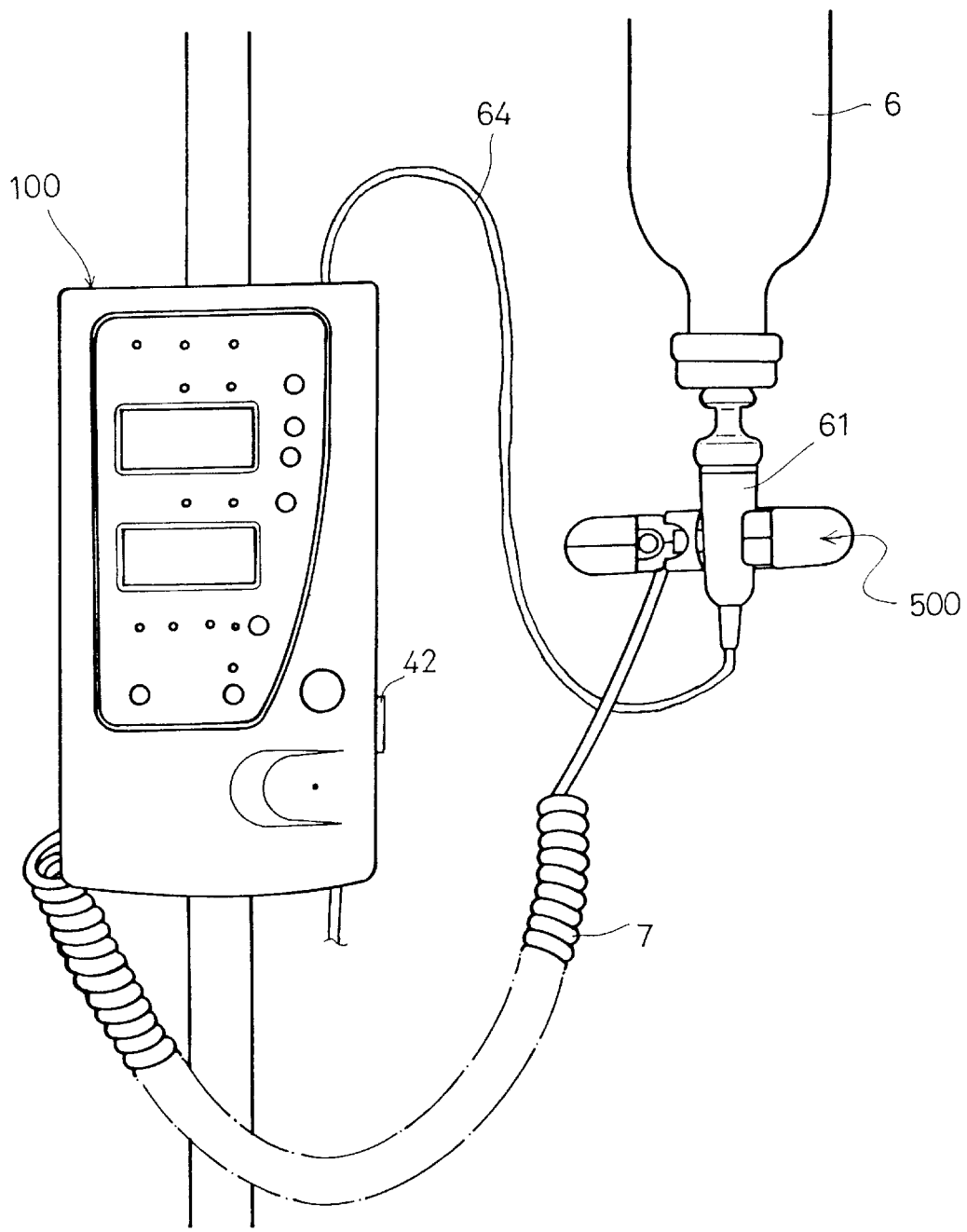
F I G. 8

INFUSION BOTTLE MONITOR DEVICE

BACKGROUND OF THE INVENTION

The present invention relates to an infusion bottle monitor device. More particularly, the present invention relates to a monitor device which can control the liquid flowing out of the infusion bottle precisely.

A conventional infusion bottle can contain nutrition liquids, or the conventional infusion bottle can contain medicines. The conventional infusion bottle can contain nutrition liquids with medicines also. The patients may be in malnutrition or undernourishment. The infusion bottle is suitable for intravenous saline infusion or intravenous nutrition infusion. In the total parenteral nutrition, the precise dosage of the nutrients is very important. If the patient receives too much water-insoluable nutrients such as vitamin A, vitamin D and vitamin E, the water-insoluable nutrients will accumulate in the body of the patient. The accumulation of the water-insoluable nutrients may worsen the health of the patient. However, the conventional infusion bottle cannot control the flow of the nutrition liquid precisely. The conventional infusion bottle can contain liquid medicines in order to infuse the liquid medicines into the vein of the patient. In accordance with the pharmaceutical kinetics, a predetermined dosage in a predetermined period should be continued for a long period of time. Furthermore, various medicines should have various dosages in various flow speed via the vein of the patient. However, the flow speed of the liquid medicine cannot be measured precisely. Therefore, the nurse can roughly measure the flow speed of the liquid medicine by eyes only. Now referring to FIGS. 1 and 1A, a conventional infusion bottle monitor device is connected to an infusion bottle 6. The conventional infusion bottle monitor device comprises a connection needle 60, a hollow tube 61, a control valve 62, an adjustment wheel 63, and a hose 64. The connection needle 60 is connected to the bottom of the infusion bottle 6. The hollow tube 61 is connected to the connection needle 60. The hose 64 is connected to the hollow tube 61. The adjustment wheel 63 is disposed in the control valve 62. The control valve 62 receives a portion of the hose 64. Referring to FIG. 1A, the adjustment wheel 63 can be rotated. The user can rotate the adjustment wheel 63 until the adjustment wheel 63 is pressed against the hose 64. When the hose 64 is pressed by the adjustment wheel 63, the flow speed of the liquid medicine in the hose 64 will be slow down. Therefore, the flow speed of the liquid medicine can be controled by the adjustment wheel 63. However, the control valve 62 may be loosened after a long period of usage. If the control valve 62 is loosened, the flow speed of the liquid medicine in the hose 64 cannot be controlled precisely. Furthermore, the flow speed of the liquid medicine can be measured roughly by eyes only. Since the conventional infusion bottle monitor device cannot display the flow speed nor alarm the user at all, the nurse has to check the conventional infusion bottle monitor device every few hours. If the predetermined dosage of the medicine in a predetermined period cannot be maintained for a long period of time, the patient will be in danger.

SUMMARY OF THE INVENTION

An object of the present invention is to provide an infusion bottle monitor device which can control the liquid flowing out of the infusion bottle precisely.

Accordingly, an infusion bottle monitor device comprises an electric circuit module, a sensing module, and a wire connected to the electric circuit module and the sensing module. The electric circuit module comprises a microprocessing system. The sensing module has a sensing system to output a sensing signal into the microprocessing system. A micromotion control system is disposed in the electric circuit module. The electric circuit module controls a motion of the micromotion control system. A hose is connected to a hollow tube. The hollow tube is connected to an infusion bottle. The sensing module is disposed on the hollow tube. A plurality of clamp devices are disposed on a lateral of the electric circuit module. An opening is formed on the lateral of the electric circuit module. A support frame is disposed on the lateral of the electric circuit module pivotally. A positioning plate is disposed on the support frame. A lock device is disposed on the support frame. The micromotion control system has a hollow casing, a motor, a driven rotor, a base cover, and a push key. The hollow casing has two lugs, a screw rod, and an oblong hole receiving the push key. The motor is disposed in the hollow casing. The motor has a rotating shaft. The driven rotor has a pivot rod, a first protruded bar, a second protruded bar, and a recess hole receiving the rotating shaft. The base cover has a U-shaped groove receiving the pivot rod. The push key has a post. A coiled elastic element encloses the push key. The motor rotates the driven rotor step by step. The driven rotor contacts the push key. The base cover covers a bottom of the hollow casing. A protruded plate is disposed in the lateral of the electric circuit module to position the support frame pivotally. An adjustment screw is disposed in the support frame.

BRIEF DESCRIPTION OF THE DRAWINGS

FIG. 3 is a perspective view of a support frame and a lock device of a preferred embodiment in accordance with the present invention;

FIG. 8 is a front elevational view of an infusion bottle monitor device of a preferred embodiment in accordance with the present invention.

DETAILED DESCRIPTION OF THE INVENTION

Figure 1A:
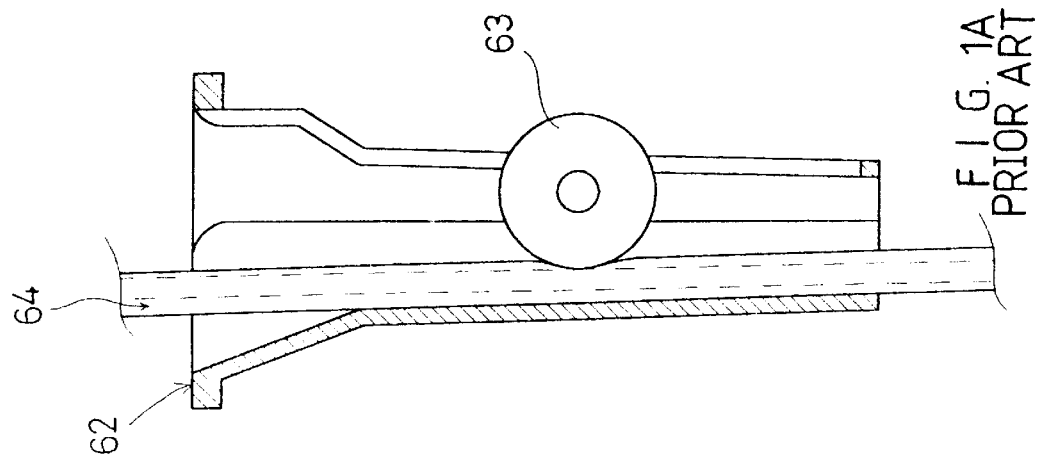
FIG. 1A is a sectional view of a control valve of the prior art.
Figure 1:
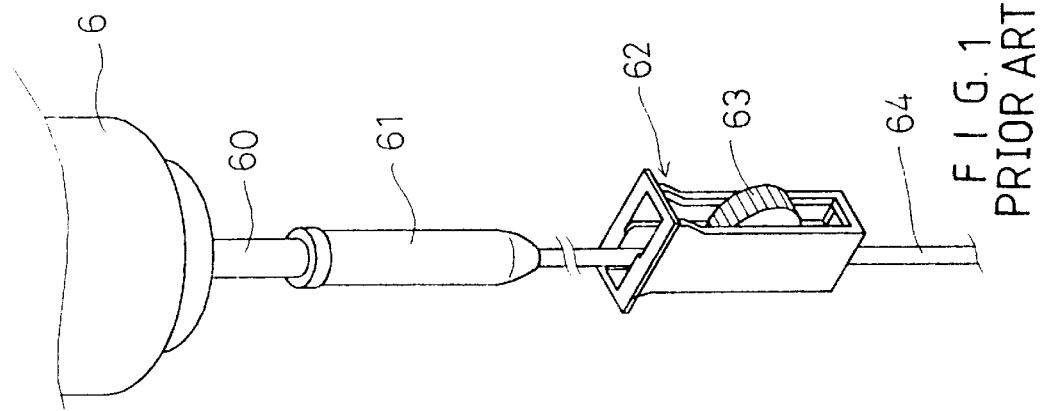
FIG. 1 is a perspective view of a conventional infusion bottle monitor device of the prior art.
Figure 2:
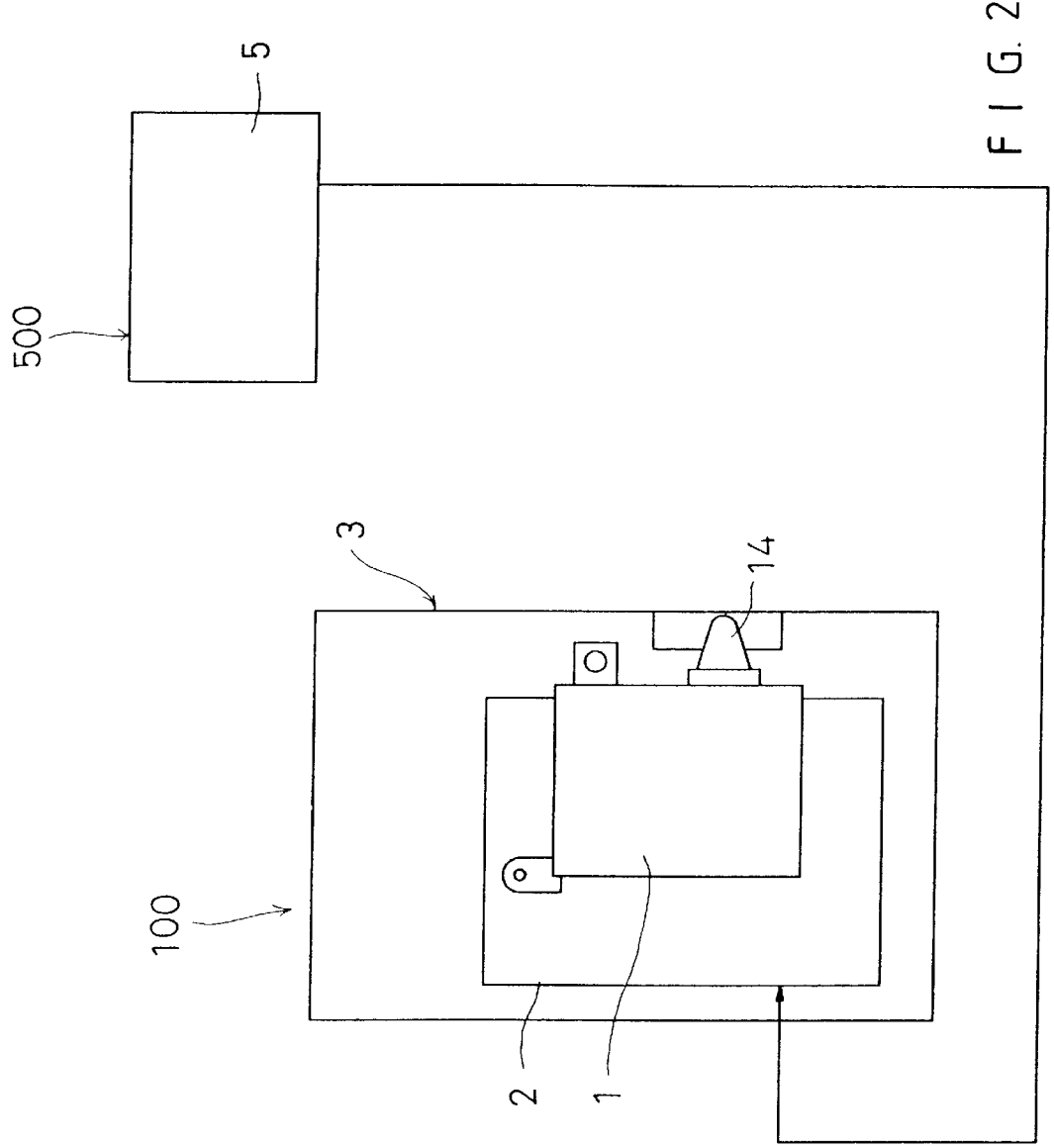
FIG. 2 is a schematic view illustrating the relationship among various systems of an infusion bottle monitor device of a preferred embodiment in accordance with the present invention.
Figure 4:
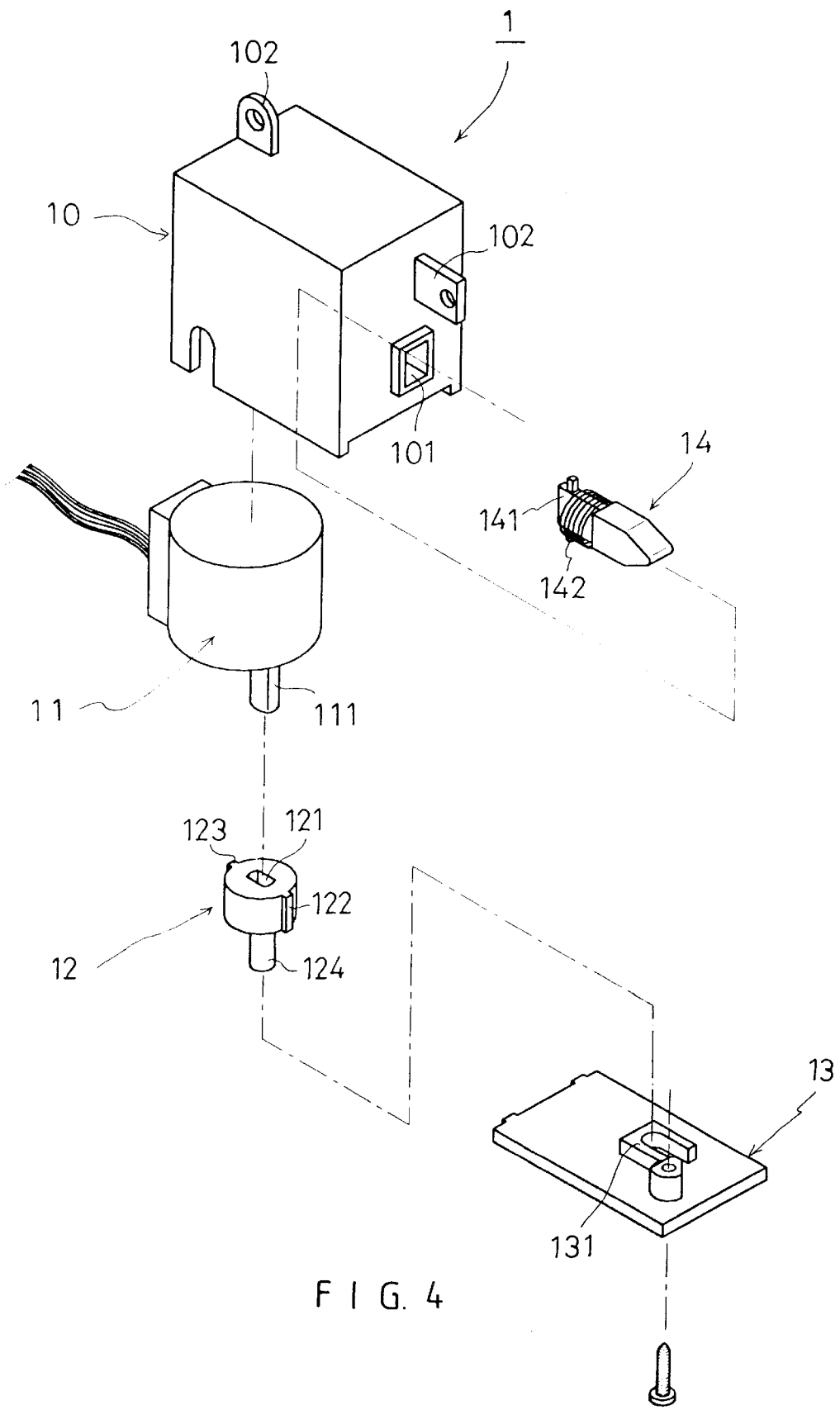
FIG. 4 is a perspective exploded view of a micromotion control system of a preferred embodiment in accordance with the present invention.

Referring to FIGS. 2 to 4 and 8, an infusion bottle monitor device comprises an electric circuit module 100, a sensing module 500, and a wire 7 connected to the electric circuit module 100 and the sensing module 500. The electric circuit module 100 comprises a microprocessing system 2 and a screen display (not shown in the figures). The sensing module 500 has a sensing system 5 to output a sensing signal into the microprocessing system 2. A micromotion control system 1 is disposed in the electric circuit module 100. The electric circuit module 100 controls a motion of the micromotion control system 1. A hose 64 is connected to a hollow tube 61. The hollow tube 61 is connected to an infusion bottle 6. The sensing module 500 is disposed on the hollow tube 61. A plurality of clamp devices 31 are disposed on a lateral 3 of the electric circuit module 100. An opening 30 is formed on the lateral 3 of the electric circuit module 100. A support frame 4 is disposed on the lateral 3 of the electric circuit module 100. A positioning plate 40 is disposed on the support frame 4. A lock device 42 is disposed on the support frame 4.

The micromotion control system 1 has a hollow casing 10, a motor 11, a driven rotor 12, a base cover 13, and a push key 14. The hollow casing 10 has two lugs 102, a screw rod 103, and an oblong hole 101 receiving the push key 14. The motor 11 is disposed in the hollow casing 10. The motor 11 has a rotating shaft 111. The driven rotor 12 has a pivot rod 124, a first protruded bar 122, a second protruded bar 122, and a recess hole 121 receiving the rotating shaft 111. The base cover 13 has a U-shaped groove 131 receiving the pivot rod 124. The push key 14 has a post 141. A coiled elastic element 142 encloses the push key 14. The motor 11 rotates the driven rotor 12 step by step. The driven rotor 12 contacts the push key 14. The base cover 13 covers a bottom of the hollow casing 10. A protruded plate 32 is disposed in the lateral 3 of the electric circuit module 100 to position the support frame 4 pivotally. An adjustment screw 41 is disposed in the support frame 4 against the positioning plate 40.

Figure 5:
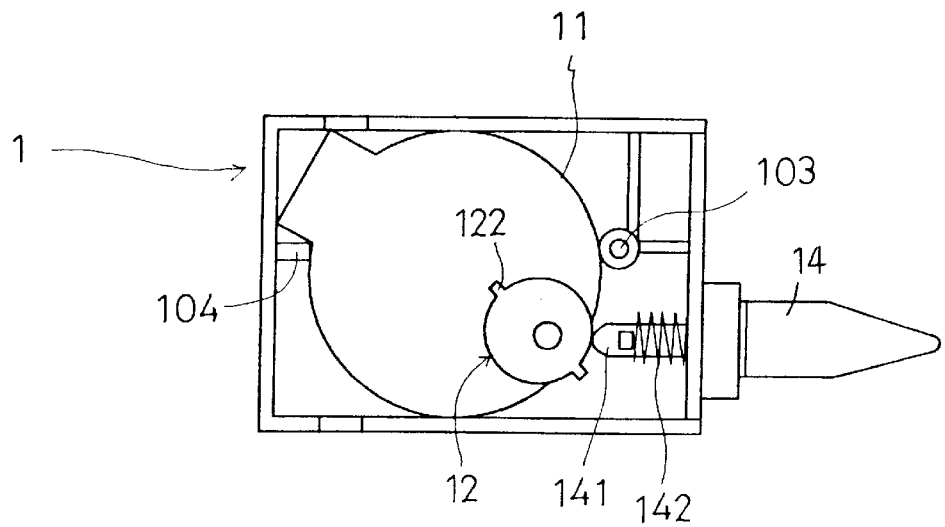
FIG. 5 is a first schematic view illustrating an operation of a micromotion control system of a preferred embodiment in accordance with the present invention.
Figure 5A:
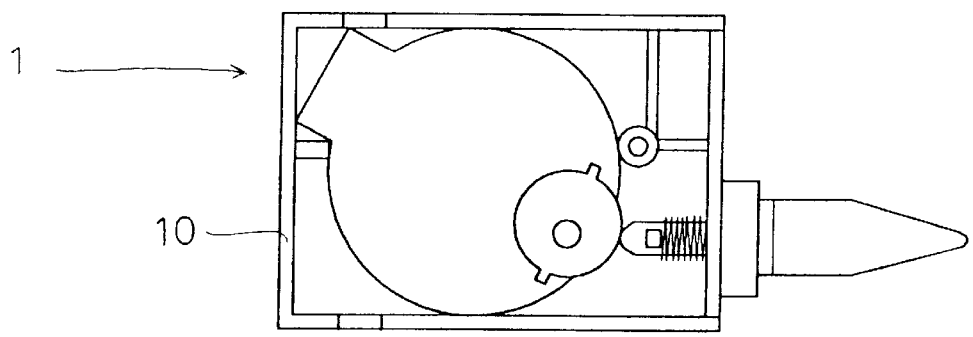
FIG. 5A is a second schematic view illustrating an operation of a micromotion control system of a preferred embodiment in accordance with the present invention.
Figure 5B:
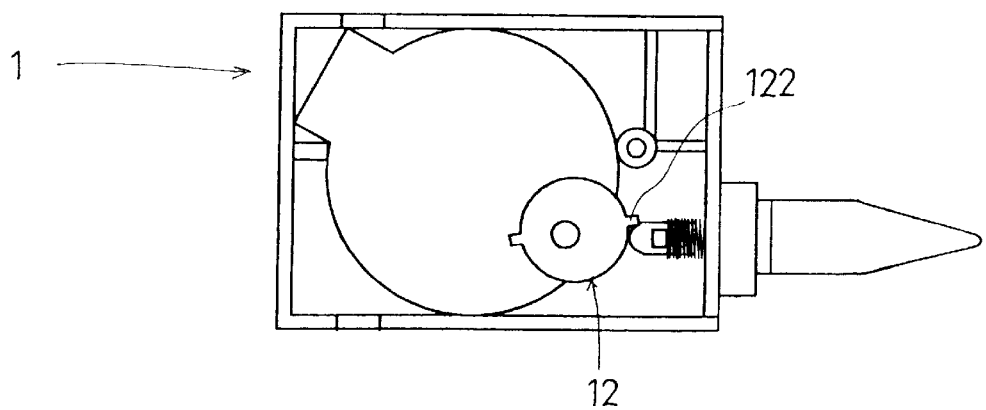
FIG. 5B is a third schematic view illustrating an operation of a micromotion control system of a preferred embodiment in accordance with the present invention.
Figure 6:
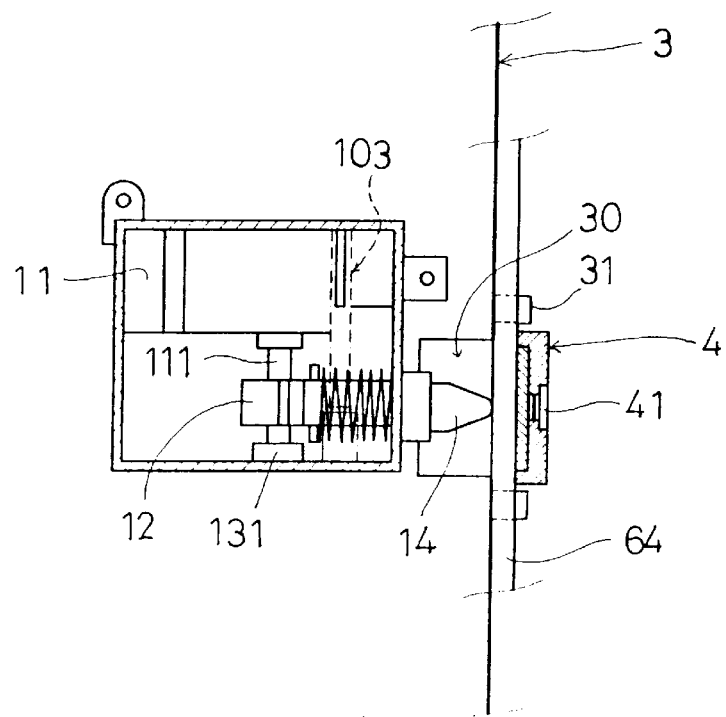
FIG. 6 is a schematic view of a micromotion control system before the micromotion control system presses against a hose.
Figure 6A:
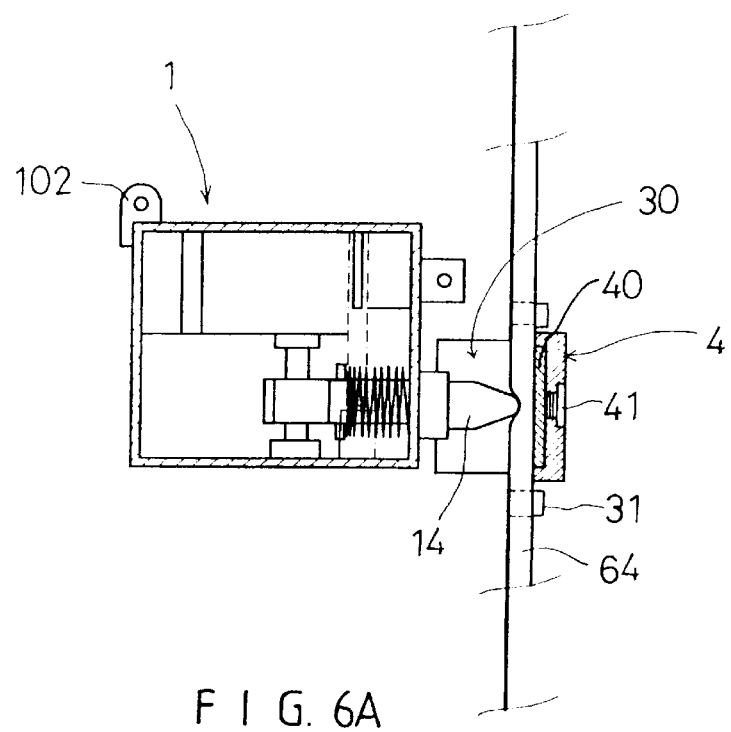
FIG. 6A is a schematic view of a micromotion control system while the micromotion control system presses against a hose.
Figure 7:
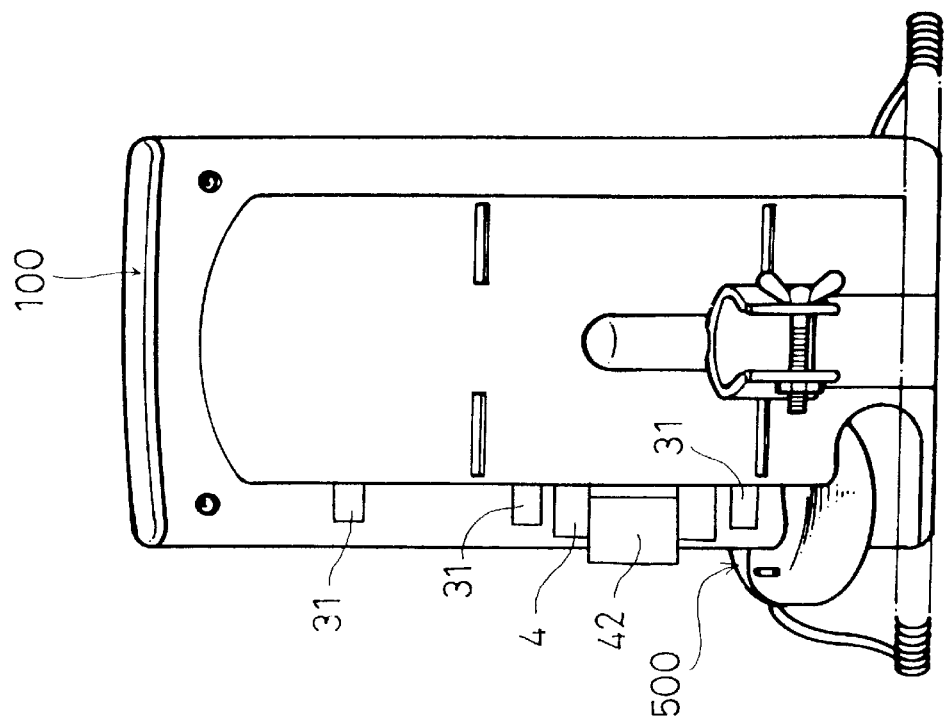
FIG. 7 is a partially rear elevational view of an infusion bottle monitor device of a preferred embodiment in accordance with the present invention.

Referring to FIGS. 5 to 5B, the driven rotor 12 drives the push key 14 to move toward the support frame 4 (as shown in FIGS. 6 and 6A).

Referring to FIGS. 6 and 6A, a portion of the hose 64 is disposed between the push key 14 and the positioning plate 40. The push key 14 can press against the hose 64. The adjustment screw 41 can adjust the position of the positioning plate 40.

The present invention is not limited to the above embodiment but various modification thereof may be made. Furthermore, various changes in form and detail may be made without departing from the scope of the present invention.

I claim:

1. An infusion bottle monitor device comprising:

an electric circuit module, a sensing module, and a wire connected to the electric circuit module and the sensing module, the electric circuit module comprising a microprocessing system, the sensing module having a sensing system to output a sensing signal into the microprocessing system, a micromotion control system disposed in the electric circuit module, a hose connected to a hollow tube, the sensing module disposed on the hollow tube, an opening formed on a lateral of the electric circuit module, a protruded plate disposed in the the lateral of the electric circuit module, a support frame positioned by the protruded plate pivotally, a positioning plate disposed on the support frame, the micromotion control system having a hollow casing, a motor, a driven rotor, a base cover, and a push key, the hollow casing having two lugs, a screw rod, and an oblong hole receiving the push key, the motor disposed in the hollow casing, the motor having a rotating shaft, the driven rotor having a pivot rod, a first protruded bar, a second protruded bar, and a recess hole receiving the rotating shaft, the base cover having a U-shaped groove receiving the pivot rod, the push key having a post, a coiled elastic element enclosing the push key, the motor rotating the driven rotor step by step, the driven rotor contacting the push key, the base cover covering a bottom of the hollow casing, a protruded plate disposed in the lateral of the electric circuit module to position the support frame pivotally, and an adjustment screw disposed in the support frame against the positioning plate.

* * * * *